(12) United States Patent
Hocken et al.

(10) Patent No.: US 8,677,803 B2
(45) Date of Patent: Mar. 25, 2014

(54) PARTICULATE MATTER DETECTION METHOD FOR A PARTICULATE MATTER SENSOR

(75) Inventors: Lary R. Hocken, Davison, MI (US); Charles S. Nelson, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 239 days.

(21) Appl. No.: 13/169,283

(22) Filed: Jun. 27, 2011

(65) Prior Publication Data

US 2012/0324982 A1 Dec. 27, 2012

(51) Int. Cl.
*G01N 37/00* (2006.01)

(52) U.S. Cl.
USPC ........................................ 73/28.01; 73/28.02

(58) Field of Classification Search
USPC .................... 73/23.33, 28.02, 31.01
See application file for complete search history.

(56) References Cited

U.S. PATENT DOCUMENTS

| 7,275,415 | B2 * | 10/2007 | Rhodes et al. ............... 73/28.01 |
| 2007/0089399 | A1 * | 4/2007 | Rhodes et al. .................. 60/278 |
| 2007/0264158 | A1 * | 11/2007 | Schmidt et al. ................. 422/94 |
| 2008/0053067 | A1 * | 3/2008 | Schmidt et al. ................. 60/276 |
| 2008/0282769 | A1 | 11/2008 | Nelson |
| 2008/0283398 | A1 | 11/2008 | Nelson et al. |
| 2009/0126458 | A1 | 5/2009 | Fleischer et al. |
| 2009/0139081 | A1 | 6/2009 | Nelson |
| 2010/0031733 | A1 * | 2/2010 | Bollinger et al. ............ 73/28.04 |

* cited by examiner

*Primary Examiner* — Daniel S Larkin
*Assistant Examiner* — Irving A Campbell
(74) *Attorney, Agent, or Firm* — Mark H. Svobodn (57) ABSTRACT

A method of detecting particulate matter on a particulate matter sensor includes the steps of measuring an electrical characteristic associated with the sensor, determining a value corresponding to the impedance across the sensor, and compensating the impedance for the temperature at which it was determined. The method further includes determining an estimate of the total amount of particulate matter accumulated while limiting the effects of large particles captured on the sensor or blown off the sensor. The information produced by the method may be used to provide diagnostic information regarding a particulate control system.

6 Claims, 6 Drawing Sheets

PARTICULATE MATTER DETECTION METHOD FOR A PARTICULATE MATTER SENSOR

BACKGROUND OF THE INVENTION

Soot sensors, also known as particulate matter (PM) sensors, are often used in vehicles having diesel engines. A particulate matter sensor may be located upstream from a diesel particulate filter (DPF), where the sensor is exposed to exhaust flow from the engine having soot particles entrained in the exhaust gas. Alternatively, a particulate matter sensor may be located in a gas stream downstream from a diesel particulate filter (DPF), where the sensor is used to monitor the proper operation of the particulate filter.

A known method of sensing soot uses a particulate matter sensor having two electrodes that are spaced from one another. In the absence of soot, there is very low electrical conductivity between the electrodes. As soot accumulates on the surface of the sensor, soot particles act to bridge the gap between the electrodes. Because the soot particles are electrically conductive, the conductivity between the electrodes increases, and this change in conductivity can be related to the amount of soot in the gas stream. Sensors that operate according to this principle are disclosed in U.S. patent application Ser. No. 11/749,262 published as US Patent Application Publication 2008/0283398, U.S. patent application Ser. No. 11/750,883 published as US Patent Application Publication 2008/0282769, and U.S. patent application Ser. No. 11/998,238 published as US Patent Application Publication 2009/0139081, the contents of all of which are hereby incorporated by reference in their entirety.

Government regulations require that the vehicle system must be able to detect when a DPF has failed. The particulate matter sensor algorithm determines this by measuring the rate of soot that passes the sensing element. The particulate matter sensing environment may contain sources of significant noise. These noise sources are primarily voltage-based noise (i.e. EMI or conducted ground noise) and soot based noise (i.e. large particulate matter particles or agglomerate particulate matter loss). The noise on the particulate matter sensor signal can interfere with the ability to detect when a DPF has failed.

Accordingly, the inventors herein have recognized a need for an improved sensing system having a particulate matter sensor that reduces and/or eliminates the foregoing deficiencies.

BRIEF SUMMARY OF THE INVENTION

To accurately measure the soot accumulation rate, this noise must be filtered out. This invention focuses on methods of eliminating noise to accurately measure soot.

DETAILED DESCRIPTION OF THE INVENTION

At the outset of the description, it should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). It is noted that the terms "left", "right", "horizontal", "vertical", "bottom", and "top" are used herein, unless otherwise noted, merely for convenience of description, and are not limited to any one position or spatial orientation. Finally, unless defined otherwise, technical and scientific terms used herein have the same meaning as is commonly understood by one of skill in the art to which this invention belongs.

Figure 1:
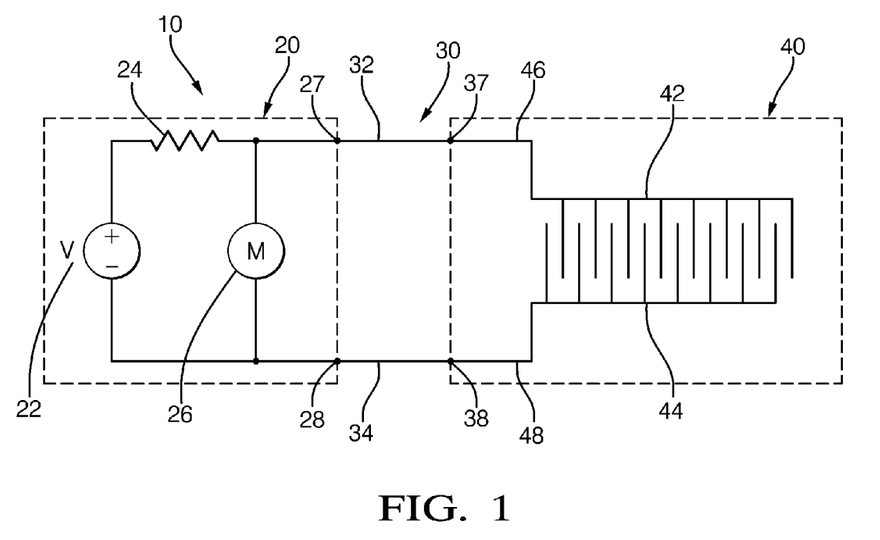
FIG. 1 is an electrical schematic of a particulate matter sensing system.

FIG. 1 is an electrical schematic of a particulate matter sensing system 10. The system may be generally considered as partitioned as indicated into a controller portion 20, a wiring harness portion 30, and a sensing element portion 40. The controller portion 20 comprises a means for measuring the impedance of a circuit connected thereto. In the exemplary controller portion 20 in FIG. 1, the impedance measurement means includes a voltage source 22 that provides a voltage value $V_{supply}$, a pull-up resistor 24 having a resistance value $R_{pullup}$, and a voltage measurement means 26. While voltage source 22 is depicted in FIG. 1 as a DC source with a given polarity, it will be appreciated that voltage source 22 can alternatively be an AC source, a DC source having opposite polarity from what is depicted, or a source providing both an AC and a DC voltage component, without departing from the inventive concept described herein. The controller portion 20 electrically interfaces to the wiring harness portion 30 by connection means 27 and 28. The wiring harness portion 30 includes conductors 32 and 34. The wiring harness portion 30 electrically interfaces to the sensing element portion 40 by connection means 37 and 38. The sensing element portion 40 includes a first electrode 42 electrically connected by conductor 46 to connection means 37, and a second electrode 44 electrically connected by conductor 48 to connection means 38.

As formed on the sensing element, the first electrode 42 is electrically isolated from the second electrode 44, so that a sensing element 40 in the absence of particulate matter appears electrically as an open circuit when measured between connection means 37 and connection means 38. In the absence of particulate matter, the voltage measured by measurement means 26 will be essentially equal to $V_{supply}$, the voltage provided by voltage source 22.

The first electrode 42 and second electrode 44 are preferably shaped in the form of interdigitized fingers with a small gap therebetween. In operation, particulate matter that is deposited on the sensing element so as to bridge the gap between the electrodes 42, 44 can be detected because the particulate matter forms a conductive path bridging the normally open circuit between the electrodes 42, 44. If the resistance of the particulate matter bridging the electrodes is assigned the value $R_{particulate}$, the voltage measured by measurement means 26 will be:

$$V_{measured} = V_{supply} \frac{R_{particulate}}{R_{pullup} + R_{particulate}}$$

As particulate matter accumulates between first electrode 42 and second electrode 44, the resistance $R_{particulate}$ will decrease, and the voltage $V_{measured}$ at measurement means 26 will decrease from the maximum value of $V_{supply}$. The controller portion can thereby determine the impedance connected across connection means 27 and 28 as a function of the voltage measured between points 27 and 28.

Figure 2A:
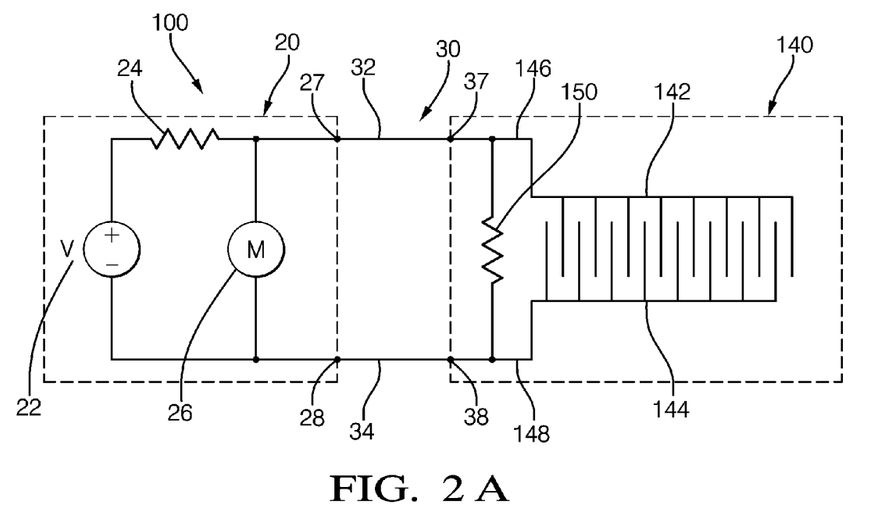
FIG. 2A is an electrical schematic of an alternative particulate matter sensing system incorporating a bias resistor.

FIG. 2A is an electrical schematic of an alternative particulate matter sensing system 100 incorporating a bias resistor, as disclosed in U.S. patent application Ser. No. 12/947,867 filed Nov. 17, 2010 titled "SELF DIAGNOSTICS OF A PARTICULATE MATTER SENSOR", the contents of which are incorporated by reference in their entirety. Controller portion 20 and wiring harness portion 30 are essentially the same as in the system 10 in FIG. 1. The sensing element portion 140 includes a first electrode 142 electrically connected by conductor 146 to connection means 37, and a second electrode 144 electrically connected by conductor 148 to connection means 38. The sensing element portion 140 in FIG. 2A contains an additional bias resistor 150 having a resistance value of $R_{bias}$ electrically connected between conductors 146 and 148. The resistance of the sensing element $R_{sensor}$ as measured between connection means 37 and connection means 38 is the parallel combination of $R_{bias}$ and the resistance resulting from particulate matter bridging the gap between the first electrode 142 and the second electrode 144. $R_{sensor}$ can be represented mathematically as:

$$R_{sensor} = \frac{R_{bias} \times R_{particulate}}{R_{bias} + R_{particulate}}$$

In the absence of particulate matter on sensing element 140, the term $R_{particulate}$ is very large compared to $R_{bias}$, and the effective sensor resistance $R_{sensor}$ is essentially equal to $R_{bias}$. This condition provides the maximum resistance value of $R_{sensor}$. As particulate matter accumulates so as to bridge the gap between the first electrode 142 and the second electrode 144, the effective sensor resistance $R_{sensor}$ will decrease from its maximum value of $R_{bias}$.

For the particulate matter sensing system 100 depicted in FIG. 2A, the voltage measured by measurement means 26 will be:

$$V_{measured} = V_{supply} \frac{R_{sensor}}{R_{pullup} + R_{sensor}}$$

In the absence of particulate matter, the value of $R_{sensor}$ will be at its maximum and will essentially equal $R_{bias}$. Under this condition, the voltage measured by measurement means 26 will be:

$$V_{measured} = V_{supply} \frac{R_{bias}}{R_{pullup} + R_{bias}}$$

Figure 2B:
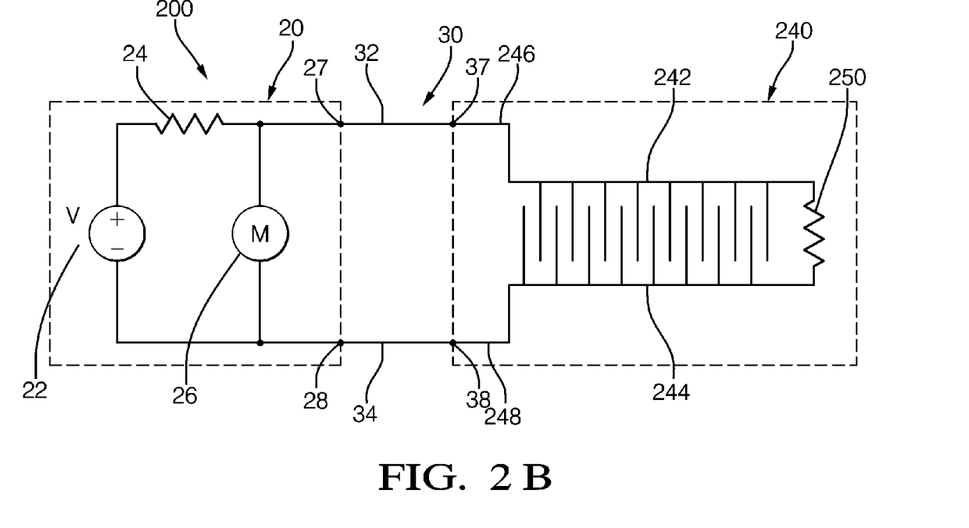
FIG. 2B is an electrical schematic of an alternative particulate matter sensing system incorporating a bias resistor in an alternative configuration.

FIG. 2B is an electrical schematic of an alternative particulate matter sensing system 200. The system 200 of FIG. 2B differs from the system 100 of FIG. 2A in that the bias resistor 250 is located remote from the connection means 37 and 38. It will be appreciated that the bias resistor 250 is still electrically in parallel with the sensing electrodes 242, 244, and that the foregoing equations presented with respect to FIG. 2A also apply to the configuration of FIG. 2B.

Figure 3:
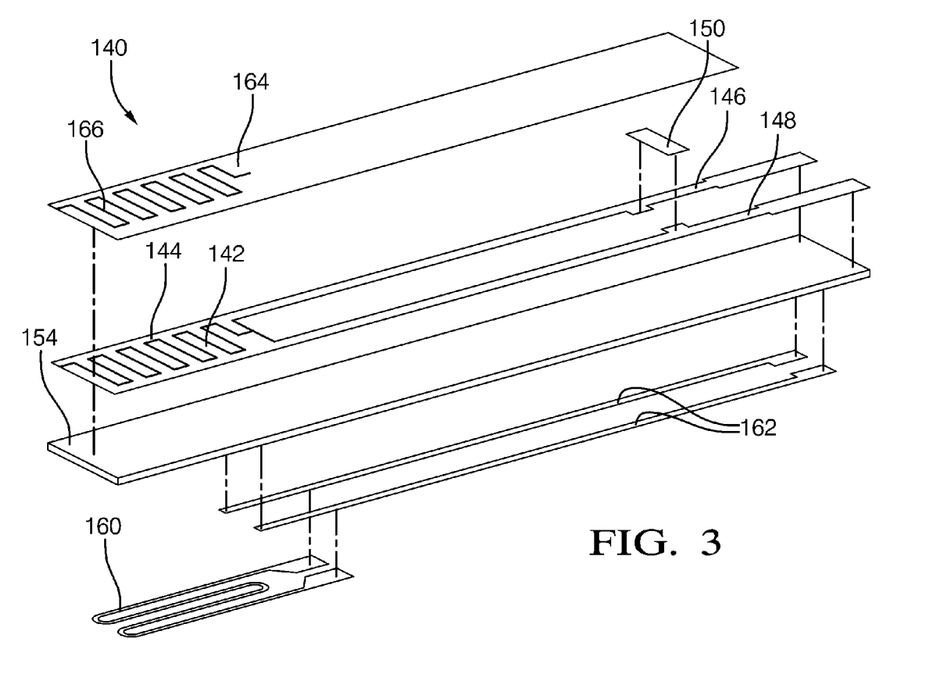
FIG. 3 is an exploded perspective view of a sensing element as found in the particulate matter sensing system of FIG. 2A.

FIG. 3 is an exploded perspective view of the sensing element 140 of FIG. 2A. The sensing element 140 includes an electrically insulating substrate 154. While shown as a single layer, it will be appreciated that substrate 154 may be formed by laminating together a plurality of layers. Conductive material disposed on one surface of substrate 154 is patterned to form conductors 146 and 148 and electrodes 142 and 144. Resistor material to form bias resistor 150 is deposited so as to form a resistive path between conductors 146 and 148. A protective layer 164 may also be included to protect the conductive material that forms electrodes 142 and 144, as well as portions of the conductors 146, 148 that may be exposed to abrasive particles in the gas stream being measured. The protective layer 164 includes an open area 166 exposing the gap between the electrodes 142 and 144 to allow particulate matter to bridge the electrodes 142 and 144. The protective layer 164 may also extend to cover bias resistor 150.

A particulate matter sensor may also include a heating means that is controllable to raise the temperature in the vicinity of the electrodes 142, 144 on the sensing element. Raising the temperature sufficiently will result in the particulate matter being removed from the surface of the sensing element, thereby restoring the resistance of the area between the sensing electrodes 142, 144 to a high resistance or essentially open circuit condition. This open circuit condition appears electrically in parallel with the bias resistor 150, so that the total resistance measured between connection means 37 and connection means 38 is restored to $R_{bias}$. The sensing element 140 depicted in FIG. 3 includes a heater 160 and heater leads 162, on the opposite surface of the substrate from the electrodes 142, 144. The heater 160 is positioned to allow the heater 160 to clean the particulate matter from the vicinity of the electrodes 142, 144 when the heater 160 is electrically powered by supplying current through heater leads 162.

Figure 4A:
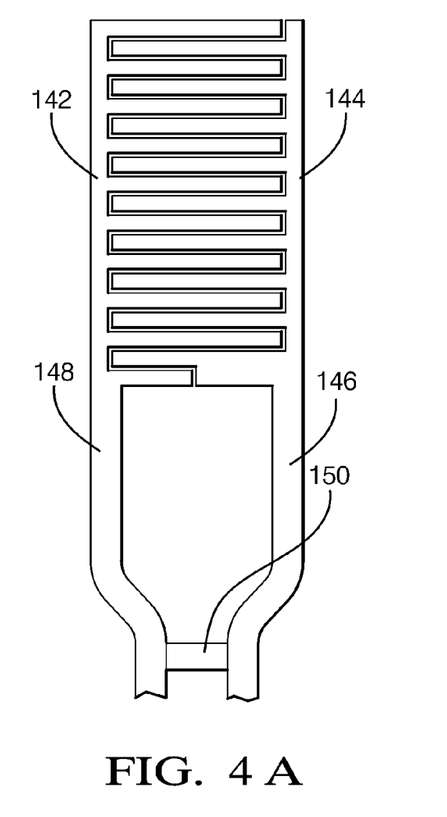
FIG. 4A is a plan view of a sensing element as found in the particulate matter sensing system of FIG. 2A.

FIG. 4A is a plan view of a conductor and resistor pattern of a sensing element 140 as depicted in FIG. 2A and FIG. 3. Bias resistor 150 is located remote from the first electrode 142 and the second electrode 144 to minimize heating of the bias resistor 150 when the heater (not shown) is activated to clean the particulate matter from the vicinity of the electrodes 142, 144.

Figure 4B:
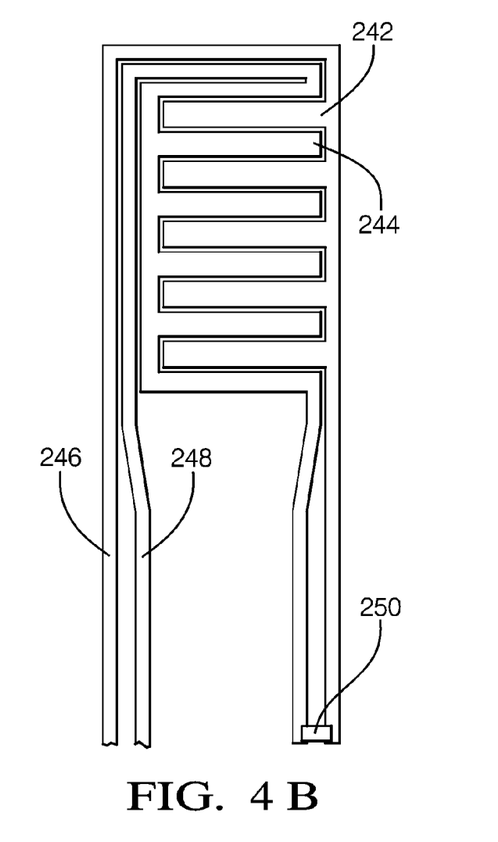
FIG. 4B is a plan view of a sensing element as found in the particulate matter sensing system of FIG. 2B.

FIG. 4B is a plan view of a conductor and resistor pattern of an alternative embodiment of a sensing element 240 as depicted in FIG. 2B. Bias resistor 250 is located remote from the first electrode 242 and the second electrode 244 to minimize heating of the bias resistor 250 when the heater (not shown) is activated to clean the particulate matter from the vicinity of the electrodes 242, 244.

It will be appreciated that the impedance indicated by a particulate matter sensor will have a maximum value equal to the resistance value of the bias resistor, in the absence of particulate matter on the sensor. As particulate matter accumulates on the sensor, the impedance will decrease from this maximum value, and the change in impedance can be detected as a change in voltage measured by the measurement means 26. The rate of change of the sensor impedance, and hence the rate of change of the measured voltage, is related to the rate of soot accumulation on the sensor.

It will be appreciated that, while it may be convenient to configure the particulate matter sensor as a part of a voltage divider circuit and to measure the voltage across the sensor as depicted in FIGS. 1, 2A, and 2B, one skilled in the art may employ other circuit configurations or measure other electrical characteristics associated with the sensor. Depending on the circuit configuration, an electrical characteristic such as a voltage across the sensor, a voltage across a circuit element in electrical connection with the sensor, a current through the sensor, electrical conductance, a current through a circuit element in electrical connection with the sensor, or the like may be used to derive information related to the effective impedance of the sensor.

For a particulate matter sensor located downstream from a diesel particulate filter, the rate of soot accumulation may provide diagnostic information related to a failure of the diesel particulate filter. Additionally, information regarding the total amount of soot accumulated on the sensor may be used to initiate regeneration of the sensor. The term "regeneration" as used herein refers to the process of applying heat to the sensor 40, 140 so as to raise the temperature of the sensor 40, 140 to a level sufficient to effect the removal of particulate matter from the surface of the sensor 40, 140 thereby restoring the sensor 40, 140 to a high impedance condition.

To provide improved information compared to using the raw unprocessed voltage information, the inventors of the present invention have determined that processing can be applied to the voltage signal derived from the particulate matter sensor. In particular, the voltage signal may contain electrical noise, for example conducted ground noise or EMI (electromagnetic interference). Additionally, the voltage signal may be influenced by soot based noise, such as abrupt, relatively large changes in voltage that result from the sensor receiving a large soot particle or from the sensor abruptly losing a large particle or agglomeration of particles. Additionally, even for a stable fixed amount of soot accumulated on the sensor, the voltage signal derived from the particulate matter sensor may be influenced by the temperature of the sensor because of the temperature coefficient of resistance of the particulate matter on the sensor.

Figure 5A:
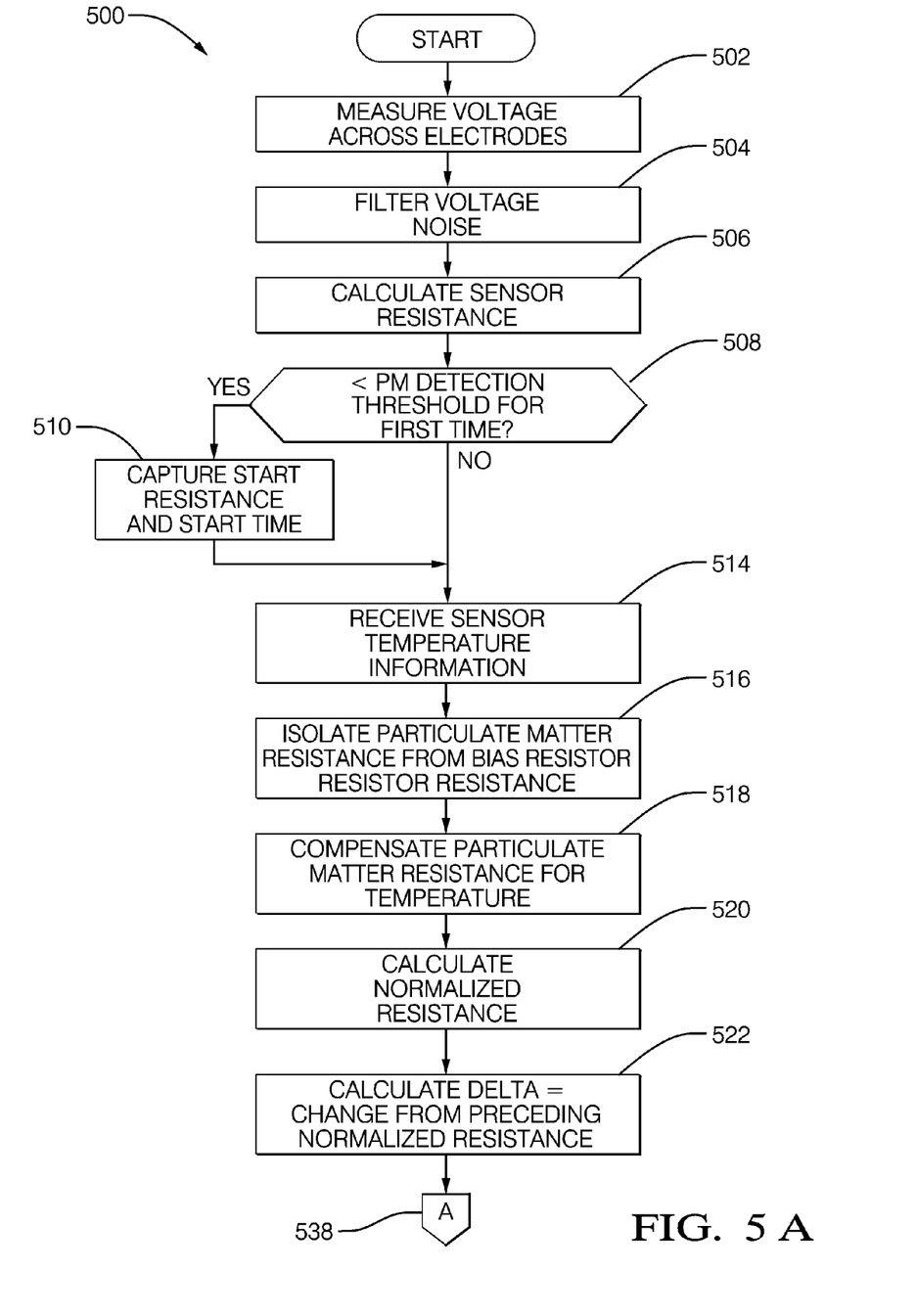
FIGS. 5A and 5B represent a flow chart of an exemplary embodiment of a particulate matter detection method incorporating aspects of the invention.
Figure 5B:
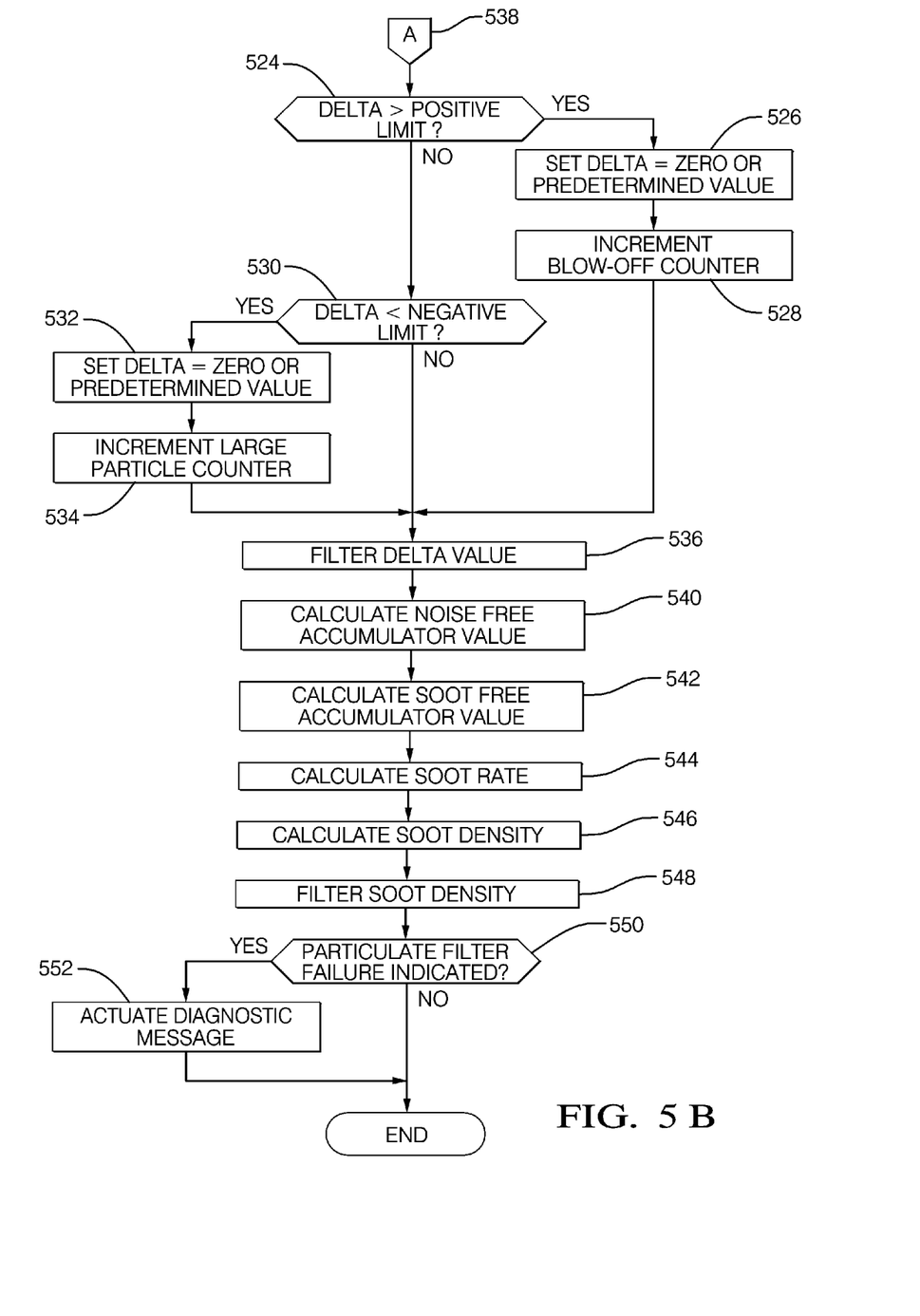

A method 500 that illustrates aspects of the present invention is depicted in the flow chart of FIGS. 5A and 5B. It is to be understood that the depicted method is to be performed repeatedly, preferably at regular defined increments, so that information about particulate matter accumulation over time can be obtained. Several of the items of information determined during execution of the method 500 depicted in FIGS. 5A and 5B are shown plotted vs. time in FIG. 6. Reference to traces in FIG. 6 will be made in the course of describing the exemplary method 500.

Figure 6:
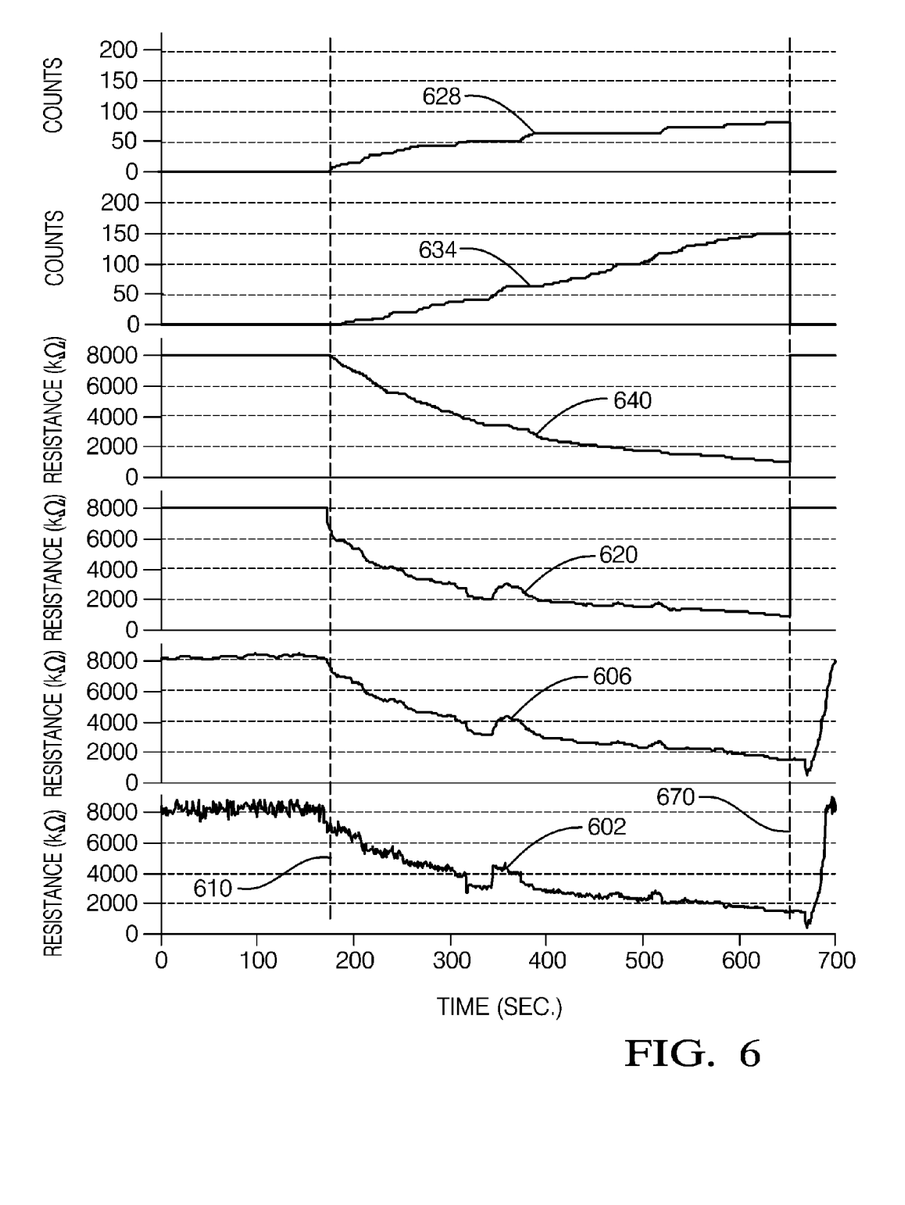
FIG. 6 is a chart illustrating signals that may be observed in a particulate matter detection method incorporating aspects of the invention.

The exemplary method 500 includes a step 502 in which the voltage is measured by measurement means 26 across the sensor electrodes (42, 44 in FIG. 1 or 142, 144 in FIG. 2A or 242, 244 in FIG. 2B). While not necessarily a required step of the exemplary method, it will be appreciated that the resistance of the particulate matter corresponding to a measured voltage can readily be determined knowing the values of the applied voltage from voltage source 22, the pull-up resistor 24, and the bias resistor 150. Trace 602 in FIG. 6 illustrates the effective resistance reading corresponding to voltage readings made in step 502.

The measured voltage value obtained in step 502 is filtered in step 504 to reduce noise on the voltage signal. The amount of filtering applied to the voltage signal may advantageously be adapted according to the level of particulate matter on the sensor 40, 140. For example, when there is no particulate matter sensed across the electrodes, heavier filtering may be applied to minimize the effects of electromagnetic interference (EMI). Once soot has been detected on the sensor 40, 140, the filtering may be reduced to improve the responsiveness of the sensor to changes in particulate matter on the sensor 40, 140. The filtering may be further reduced during regeneration of the sensor 40, 140 so that the signal representing the resistance across the electrodes 42, 44 or 142, 144 will quickly return to the "open circuit" condition. The type of filter used (e.g. low pass, Chebyshev, etc.) may be dependent on the source and periodicity of the noise to be filtered.

In step 506, the sensor resistance is calculated from the filtered voltage level, the voltage of source 22, and the value of pull-up resistor 24. For a sensor that includes a bias resistor, such as sensor 140 in FIG. 2A or sensor 240 in FIG. 2B, the sensor resistance is the parallel combination of the bias resistor 150 or 250 and the resistance of the particulate matter accumulated on the sensor. Trace 606 in FIG. 6 illustrates the calculated resistance vs. time calculated by filtering the voltage used to generate trace 602.

When the sensor is free of particulate matter, the sensor resistance will be equal to the resistance value of the bias resistor 150. As particulate matter accumulates on the sensor, the sensor resistance will decrease from the value of the bias resistor. The first time that particulate matter is recognized as being present on the sensor in step 508, as determined by the resistance of a "clean" (new or regenerated) sensor falling below a particulate matter detection threshold for the first time, a starting resistance value and a start time value are captured in step 510. These starting resistance value and start time value will be used in determinations to be discussed in later steps. The vertical line 610 in FIG. 6 indicates the start time value when the sensor resistance falls below a detection threshold.

In step 514, exhaust temperature information is received. This information will be used to compensate the particulate matter resistance for the temperature coefficient of resistance of the particulate matter, as will be discussed with respect to step 518.

As previously indicated, the measured sensor resistance includes the parallel combination of the resistance of the particulate matter and the fixed bias resistance. In step 516 the known bias resistance and the total sensor resistance previously determined in step 506 are used to determine the effective particulate matter resistance, that is, the resistance which is required in parallel with the bias resistance to produce the determined sensor resistance.

The material comprising the particulate matter has been determined to have a non-negligible temperature coefficient of resistance (TCR). As a result, a given fixed amount (mass) of particulate matter on the sensor may exhibit different resistance measurements if the measurements are taken at different temperatures. To reduce this source of variability, step 518 compensates the particulate matter resistance for the temperature at which the measurement was taken (as received in step 514), using the predetermined TCR of the particulate matter. As an example of this compensation, the temperature and TCR may be used to determine what the resistance of the particulate matter would be if it were measured at a given temperature, for example 150° C. This temperature compensation step 518 may be bypassed under certain specific conditions, for example when the sensor is being regenerated.

In step 520, a value defined as the "Normalized Resistance" is calculated as the parallel combination of the fixed bias resistor and the temperature compensated particulate matter resistance determined in step 518. This has been determined to be advantageous so that ensuing calculations do not have to deal with infinite resistance conditions such as the resistance between the electrodes of a clean sensor. Trace 620 in FIG. 6 depicts the normalized temperature corrected resistance corresponding to the filtered resistance given in trace 606.

As previously indicated, the depicted method is to be performed repeatedly, preferably at regular defined increments, so that information about particulate matter accumulation over time can be obtained. A delta value representing the difference between the current and preceding values of Normalized Resistance is calculated in step 522. As long as the method described in FIGS. 5A and 5B is performed at equal time intervals, the actual time interval serves as a scaling factor in interpreting the results but does not need to enter into the calculations. Alternately, the method may be performed at non-equal time intervals, but in this case the actual elapsed time between samples should be accounted for, such as by dividing the calculated delta value by the elapsed time value. It will be appreciated that the delta value corresponds to a change in the sensor resistance, and accordingly to a change in the amount of particulate matter accumulated on the sensor during the time since the previous measurement.

Connector block 538 in FIGS. 5A and 5B merely indicates that the flow chart is divided onto two pages with block 538 indicating the same point in the method on each page, that is, step 524 in FIG. 5B follows step 522 in FIG. 5A in this discussion of an embodiment.

Step 524 in FIG. 5B compares the calculated delta value to a predetermined positive limit. It will be appreciated that a positive value of delta is indicative of an increase in resistance, such as would be caused by a loss of particulate matter from the sensor. An increase in resistance exceeding a positive threshold may result, for example, from a large particle being blown off the sensor. If the result of the comparison in step 524 is that delta exceeds the positive threshold, step 526 sets the value of delta to zero or to another predetermined calibration value for use in ensuing calculations. The predetermined calibration value in step 526 may be a fixed resistance, or alternately it may be a percentage of the current normalized resistance value. Step 528 increments a blow-off counter that keeps track of the number of occurrences of large particle blow-off events. An excessive number of blow-off counts may be used as an indication of invalidity of the resistance-to-mass transfer function. Trace 628 in FIG. 6 depicts a blow-off count generated from the resistance behavior depicted in trace 620. The blow-off count is reset during regeneration.

If the comparison in step 524 does not detect a delta value exceeding the positive limit, step 530 compares the calculated delta value to a predetermined negative limit. It will be appreciated that a negative value of delta is indicative of a decrease in resistance, due to additional particulate matter accumulating on the sensor. If the value of delta is more negative than a predetermined negative threshold may be indicative of a particularly sudden accumulation of particulate matter, such as a particularly large soot particle adhering to the sensor. If the result of the comparison in step 530 is that delta is more negative than the negative limit, step 532 sets the value of delta to zero or to another predetermined value for use in ensuing calculations. The predetermined calibration value in step 532 may be a fixed resistance, or alternately it may be a percentage of the current normalized resistance value. Step 534 increments a soot noise counter that keeps track of the number of occurrences of large particle collection events. Trace 634 in FIG. 6 depicts a large soot noise count generated from the resistance behavior depicted in trace 620. The large soot noise counter is reset during regeneration.

The positive comparison limit in step 524 and the negative comparison limit in step 530 may be a fixed resistance change, which has been found to be beneficial for filtering out soot noise at high resistance levels. Alternately, the comparison limits may be a percentage of the normalized resistance, which has been found to be beneficial for filtering out soot noise at low resistance levels. The calibration may include both fixed resistance and percentage comparison thresholds.

The effective delta value, which is either the actual delta calculated in step 522 or a limited delta value assigned in step 526 or 532 based on the results of the comparisons in steps 524 or 530 respectively, is filtered in step 536. The filter used in step 536 may be an equally weighted moving average filter, or it may be another type of filter that smoothes out the effects of noise in the Referring to FIG. 5B, step 540 calculates a "Noise Free Accumulator" value by adding the filtered effective delta value determined in step 536 at each sample time to the previous value of the Noise Free Accumulator. The signal from the Noise Free Accumulator is represented by trace 640 in FIG. 6. This accumulator is reset to an initial value during regeneration, and starts accumulating at the start time (610 in FIG. 6) determined in step 510. This accumulator represents the resistance of the sensor after effects of the soot-based noise has been removed.

In step 542, a Soot Mass value is calculated, representing the total mass of soot (e.g. measured in milligrams) accumulated on the sensor since the last regeneration. In one embodiment, the Soot Mass is derived by adding the product of a resistance-to-mass scaling factor and the effective delta value determined in step 536 to the previously accumulated value of the Soot Mass (soot mass integrator). In an alternate embodiment, the Soot Mass value is calculated directly from the Noise Free soot resistance, using an equation of the form:
$$\text{Soot}_{Mass} = \alpha * \text{Soot}_{resistance}^{\beta}$$
where $\alpha$ and $\beta$ are previously determined constants whose value may depend on exhaust velocity, exhaust temperature, and sensor voltage (due to electrophoretic effect). The Soot Mass value is reset to an initial value during regeneration, and starts accumulating at the start time (610 in FIG. 6) determined in step 510.

Step 544 calculates the soot accumulation rate per unit time using a real-time derivative calculation. The soot accumulation rate may be determined by dividing the soot mass accumulated during the elapsed time period by the elapsed time since the start time determined in step 510. Soot rate is expressed in units such as milligrams per second.

In step 546, the soot density in the exhaust stream is calculated by using the soot rate determined in step 544 along with exhaust flow velocity (obtained using the vehicle mass air flow rate) and air density (compensating for exhaust air temperature and barometric pressure). Soot density is expressed in units such as milligrams per cubic meter.

The soot density determined in step 546 may be noisy, due to fluctuations in the air flow measurement. Step 548 applies filtering to the soot density value determined in step 546 to reduce this noise. It has been determined that it may be advantageous to vary the effective filter time constant used, with heavier filtering being applied when no soot is detected and reduced filtering applied when soot is detected.

The exemplary method described herein determines a number of parameters that may be useful in controlling or diagnosing vehicle operation. In the example shown in FIG. 5B, the filtered soot density value is used to detect failure of a diesel particulate filter. If step 550 determines that the soot density is of a level indicative of a particulate filter failure, step 552 actuates the appropriate diagnostic message. Soot mass, soot mass rate, or time between regenerations may also be used to indicate a particulate filter failure.

It will be appreciated that other parameters determined using the method described herein may be useful to initiate other actions. For example, soot accumulation above a given threshold or soot resistance below a given threshold may be used to initiate regeneration of the sensor, as indicated at time 670 in FIG. 6. As earlier described, regeneration refers to the process of heating the sensor to raise its temperature to a level sufficient to remove soot from the surface of the sensor. As shown in FIG. 6, after initiation of regeneration at time 670 the resistance 602 derived from the raw voltage measurement begins to increase, as does the corresponding filtered resistance value 606. Certain calculated values as shown in traces 620 and 640 in FIG. 6, as well as the counts shown as traces 634 and 638, are reset to their respective initial values at the initiation of regeneration at time 670. As described earlier, the time constants of certain filters may be set to different values at the initiation of regeneration.

A method including aspects of the present invention offers several advantages over merely applying heavy filtering to a voltage signal derived from a particulate matter sensor. Simple filtering may degrade response time to detect a failure of a diesel particulate filter. Additionally, merely filtering the voltage signal without accounting for the temperature of the soot does not allow compensation for the temperature coefficient of resistance of the soot, thereby degrading the accuracy of the determination of the soot accumulation rate. Large sudden changes in voltage may be caused by the abrupt capture of a large soot particle on the sensor or by the abrupt blow-off of a large amount of soot. The method presented herein provides improvements to compensate for the above-mentioned factors.

While this invention has been described in terms of embodiments thereof, it is not intended to be so limited, but rather only to the extent set forth in the claims that follow.

The invention claimed is:

1. A method for determining particle matter accumulation between two mutually spaced electrodes on a particle matter sensor, the method comprising the steps of:
   (a) determining the value of an electrical characteristic associated with the sensor;
   (b) using the value of the electrical characteristic to determine a first value that corresponds to the impedance between the electrodes of the sensor;
   (c) using information relating to the temperature of the sensor to determine a second value that represents the first value normalized to a predetermined sensor temperature;
   (d) determining the rate of particulate matter accumulation as a function of the difference between successive determinations of the second value and of the elapsed time between successive determinations of the electrical characteristic of the sensor;
   (e) indicating any identified faults; and
   (f) repeating steps (a) through (e);
   further including the step of determining a filtered second value either by
   applying filtering to a plurality of successive determinations of the first value to determine a filtered first value and determining a filtered second value by using information relating to the temperature of the sensor to determine the filtered second value that represents the filtered first value normalized to the predetermined sensor temperature; or by
   applying filtering to a plurality of successive determinations of the second value to determine the filtered second value;
   wherein, if the value of the difference between successive determinations of the filtered second value is more positive than a predetermined maximum positive value, a blow-off counter is incremented.

2. The method of claim 1 further comprising the step of determining the mass of particulate matter removal corresponding to the observed difference between successive determinations of the filtered second value.

3. The method of claim 2 further including the step of restarting the method of determination of particulate matter accumulation if one of the blow-off counter or the determined mass of particulate matter removal corresponding to the observed difference between successive determinations of the filtered second value exceeds a predetermined threshold.

4. A method for determining particle matter accumulation between two mutually spaced electrodes on a particle matter sensor, the method comprising the steps of:
   (a) determining the value of an electrical characteristic associated with the sensor;
   (b) using the value of the electrical characteristic to determine a first value that corresponds to the impedance between the electrodes of the sensor;
   (c) using information relating to the temperature of the sensor to determine a second value that represents the first value normalized to a predetermined sensor temperature;
   (d) determining the rate of particulate matter accumulation as a function of the difference between successive determinations of the second value and of the elapsed time between successive determinations of the electrical characteristic of the sensor;
   (e) indicating any identified faults; and
   (f) repeating steps (a) through (e);
   further including the step of determining a filtered second value either by
   applying filtering to a plurality of successive determinations of the first value to determine a filtered first value and determining a filtered second value by using information relating to the temperature of the sensor to determine the filtered second value that represents the filtered first value normalized to the predetermined sensor temperature; or by
   applying filtering to a plurality of successive determinations of the second value to determine the filtered second value;
   wherein, if the value of the difference between successive determinations of the filtered second value is more negative than a predetermined maximum negative value, a large particulate matter counter is incremented.

5. The method of claim 4 further comprising the step of determining the mass of large particulate matter accumulation corresponding to the observed difference between successive determinations of the filtered second value.

6. The method of claim 5 further including the step of restarting the method of determination of particulate matter accumulation if one of the large particulate matter counter or the determined mass of large particulate matter accumulation corresponding to the observed difference between successive determinations of the filtered second value exceeds a predetermined threshold.

* * * * *